United States Patent [19]

Demopoulos

[11] Patent Number: 5,326,757
[45] Date of Patent: Jul. 5, 1994

[54] PHARMACEUTICALLY ACTIVE ANTIOXIDANT CONTAINING COMPOSITION AND THE METHOD OF ITS USE TO PREVENT AND TREAT RESTENOSIS FOLLOWING ANGIOPLASTY

[75] Inventor: Harry B. Demopoulos, Scarsdale, N.Y.

[73] Assignee: Health Maintenance Programs, Inc., Elmsford, N.Y.

[21] Appl. No.: 108,849

[22] Filed: Aug. 18, 1993

Related U.S. Application Data

[63] Continuation of Ser. No. 817,293, Jan. 6, 1992, abandoned.

[51] Int. Cl.$^5$ .................. A01N 45/00; A61K 31/59
[52] U.S. Cl. ...................... 514/167; 514/251; 514/276; 514/458725; 424/602; 424/451
[58] Field of Search ............... 424/602; 514/167, 251, 514/276, 458, 725, 904, 905

[56] References Cited

U.S. PATENT DOCUMENTS

| | | | |
|---|---|---|---|
| 4,454,125 | 6/1984 | Demopoulos | 514/784 |
| 4,619,829 | 10/1986 | Motschan | 514/904 |
| 5,023,235 | 6/1991 | N'Guyen et al. | 530/331 |

OTHER PUBLICATIONS

Performance Packs Jan. 5, 1991.

*Primary Examiner*—Nathan M. Nutter
*Attorney, Agent, or Firm*—Lerner, David, Littenberg, Krumholz & Mentlik

[57] ABSTRACT

The present invention relates to formulations and methods for preventing and treating restenosis following angioplasty. This is accomplished by the regimented administration of a composition which includes selected antioxidants.

18 Claims, No Drawings

PHARMACEUTICALLY ACTIVE ANTIOXIDANT CONTAINING COMPOSITION AND THE METHOD OF ITS USE TO PREVENT AND TREAT RESTENOSIS FOLLOWING ANGIOPLASTY

This is a continuation division of U.S. application Ser. No. 07/817,293 filed Jan. 6, 1992, now abandoned.

FIELD OF THE INVENTION

The present invention relates to an antioxidant containing composition and its use in the prevention and treatment of restenosis following angioplasty.

BACKGROUND OF THE INVENTION

Angioplasty is a technique whereby an artery clogged by an atherosclerotic plaque and/or thrombus is mechanically cleared. Angioplasty procedures are much less invasive and much less traumatic than conventional alternatives such as coronary bypass surgery and have gained widespread acceptance as a means of obtaining dilation or clearance of arteries. In conventional angioplasty procedures, a small balloon-tipped catheter is introduced into an artery, often using a guide wire or a catheter tube in which a collapsed balloon may be positioned at one or more points of arterial stenosis, i.e. narrowing. These balloon and catheter assemblies are often referred to as coronary balloon dilation catheters. In many cases, the catheters are designed to permit continued distal dye injections through the balloon to permit visual verification of proper approach to a lesion or other area in which the procedure is to be employed.

However, it is also well known that angioplasty procedures involve risks of both local and systemic thromboembolic effects, tearing of an arterial wall, and restenosis. As used herein, restenosis refers to a worsening of lumenal stenosis in an artery which is characterized by a hyperplasia of cells of the arterial wall, resulting from an injury to the arterial wall which is a direct consequence of the angioplastic procedure. In this respect, restenosis differs notably from an occlusion of the artery by an arterial atherosclerotic plaque or occlusion by thrombus. In fact, restenosis within a few months (3-6 months) after angioplasty occurs in about 25 to about 55% of patients so treated, depending on a number of variables including, but not limited to age, sex, previous angioplastic procedures, extent of the narrowing, number of arteries involved, smoking, nutrition, diabetes mellitus and activity patterns.

While not wishing to be bound by any particular theory, restenosis may result from the body's natural recuperative response to any internal injury. Specifically, restenosis might be explained as the uncontrolled accumulation of macrophage cells and platelets generally involved in the natural healing processes of the body. Macrophages are amoeboid cells and engulf tissue debris, microbes and foreign particles. Platelets are fragments of a type of bone marrow cell and do not have a nucleus; they are involved principally in blood coagulation. These cells and platelets accumulate in the area injured by angioplasty and tend to form a protective barrier to cover the inner lining of the arterial site which has had fibrotic, calcific and fatty debris pushed into the wall by the dilated balloon. The macrophage cells and platelets also begin an oxidative metabolism of arachidonic acid to form a variety of compounds including prostaglandins, thromboxane $A_2$, leucotrienes, and related oxidation products. Some of these compounds are chemo-attractants and cause platelets, macrophage cells and white blood cells to accumulate in the arterial wall at the angioplasty site. Once activated through the oxidative metabolism of arachidonic acid, the macrophage cells and platelets produce additional products including cytokines, platelet-derived growth factor, and macrophage-derived growth factor (PDGF and MDGF respectively). These cytokines and factors act to stimulate not only the further accumulation of platelets, white blood cells and macrophage cells but also the cell division of smooth muscle cells and fibroblasts. Certain prostaglandins, as well as PDGF and MDGF, are potent activators of cell mitosis and division. If left unchecked, eventual occlusion, i.e. restenosis, results in 3-6 months.

There is additional evidence to suggest that these restenosis processes may be mediated by a highly reactive class of compounds known as free radicals. Restenosis is therefore believed to involve an increase in concentrations of free radicals, beyond the level present in undamaged tissues. Free radicals contain an unpaired electron in an outer orbital and are consequently unstable and attack other molecules in order to obtain electrons to complete their electron orbitals. The hyperplasia (cell division of smooth muscle cells and fibroblasts) which characterizes restenosis may be triggered through a sequence of events initiated by the destructive free radical moieties generated by injury to the arterial wall during the angioplasty procedure. Traumatic injuries are known to cause destructive free radicals. These free radical moieties may include such molecules as perioxidized lipids and oxidized cholesterol molecules which may be generated during the metabolic conversion of arachidonic acid and other polyunsaturated lipids as previously described. Furthermore, cholesterol is more rapidly oxidized in the presence of lipid peroxides, as formed from arachidonic acid and other polyunsaturates. In addition, lipid peroxide free radicals formed in response to vascular injury increase thromboxane A2 synthesis by platelets. Thromboxane A2 is a powerful vasoconstrictor which also stimulates platelet adherence and aggregation. These phenomena, acting in concert, may explain restenosis.

It has been common to use injections of heparin and various known calcium blockers as well as such compounds as aspirin, persantine, and intravenous dextran in an attempt to minimize the complications often attendant to such angioplasty.

U.S. Pat. No. 4,820,732, issued in the name of Shell et al., suggests the application of prostaglandin E-1 to reduce dysfunction in an angioplasty procedure. Certain prostaglandin compounds have been suggested for their effectiveness in providing antiplatelet effects and antithrombotic effects.

The remaining procedures for the prevention and/or treatment of restenosis involve the use of mechanical/surgical procedures such as intravascular stenting, a procedure in which an expandable metallic sleeve is placed within the artery after angioplasty. Unfortunately this method places a patient in higher risk for acute coronary occlusion, in addition to the risks that additional surgical procedures pose.

The antioxidant properties of the tripeptide glutathione are known in the art, yet its use in human treatment has been limited to the treatment of viral infections, hepatic disorders, pernicious anemia, heavy metal poisoning, and as an adjunct to cancer chemotherapy, See, for example, U.S. Pat. Nos. 3,146,165, 4,689,347, 4,229,468 and 4,762,705. Glutathione has also been used experimentally by aerosol instillation in patients with AIDS, to suppress recurrence of severe pneumonias (Buhl, et al., The Lancet, Dec. 2, 1989 pp. 1294–1298). It has also been used in cosmetic preparations and for weight loss as disclosed in U.S. Pat. Nos. 4,229,468, 3,984,569 and 4,460,978 and as a food or cosmetic preservative. See also U.S. Pat. Nos. 4,009,264, 4,751,285, 4,761,399 and U.S. Pat. No. 5,023,235.

Vitamin C (ascorbic acid), Vitamin E (alpha tocopherol), beta carotene, (precursor to Vitamin A) and the B vitamins have been used in various multi-vitamin compositions to promote general health. Vitamins of these general classes have also been used in combination with other compounds in the treatment of rheumatic diseases, for the temporary stimulation of urine production, for desensitizing the gastro intestinal tract from food allergies, for the treatment of liver disorders, for treatment of cuts, burns and abrasions, for the treatment of inflammatory changes of the bronchial mucosa, and for relief in pain as has been disclosed in U.S. Pat. Nos. 4,619,829, 4,760,080, 4,721,716, 4,761,399, 4,784,842, 4,606,920, and 4,650,688. Vitamins have also been used in food preparations as a method for preventing rancidification.

Multivitamin and mineral supplements including bioflavonids, L-glutathione and L-cysteine have been suggested for use in preventing cancer, preventing cardiovascular and immunological disorders and for increasing longevity. See WO 91/11117. The use of dietary antioxidants together with a methionine compound to ameliorate inflammatory symptoms of respiratory disease has also been suggested. U.S. Pat. No. 4,927,850.

Despite the dramatic advances in cardiac surgery and care realized in recent years, there remains a need for effective, inexpensive, non-surgical techniques for the prevention and treatment of restenosis. In the United States, approximately 300,000 angioplasties were carried out in 1989, and a significant number of patients will restenose.

OBJECTS AND SUMMARY OF THE PRESENT INVENTION

It is an object of the present invention to provide a safe, inexpensive, non-surgical method for the prevention and treatment of restenosis following angioplasty.

It is also an object of the present invention to provide compositions which are ideally suited for this therapeutic goal.

Other objects of the present invention will be readily apparent to those of ordinary skill in the appropriate art.

In accordance with one aspect of the present invention, there is provided a method of preventing and treating restenosis in mammalian organisms, said method comprising the step of administering, in each 24 hour period, a formulation including the compounds L-ascorbic acid in reduced form, L-glutathione in reduced form, D,L-alpha tocopheryl acetate, and beta carotene, each of said compounds of said formulation being present in an amount effective to treat and to prevent the formation of restenosis, to a mammalian organism in need of such treatment.

In accordance with another aspect of the present invention, there is provided the method of preventing and treating restenosis as previously described wherein the L-ascorbic is provided in an amount of between about 6,500 and about 10,000 mg; the L-glutathione is present in an amount of between about 325 and about 500 mg; the D,L-alpha tocopheryl acetate is present in an amount of between about 600 and 1,000 IU; and the beta carotene in an amount of between about 100 and 150 mg.

In a preferred embodiment in accordance with this aspect of the present invention the formulation is administered in four substantially equal dosages, each of which is administered between about 4 and about 7 hours apart.

In accordance with another aspect of the present invention there is provided a method of preventing and treating restenosis in a mammalian organism, said method comprising the step of administering, in each 24 hour period, a formulation which includes L-ascorbic acid in reduced form, calcium carbonate, calcium D-pantothenate, L-glutathione in reduced form, D,L-alpha tocopheryl acetate, thiamine hydrochloride, pyridoxine hydrochloride, beta carotene, niacinamide, niacin, riboflavin, cyanocobalamin, and cholecalciferol, each of the compounds of the formulation being present in an amount effective to treat and to prevent the formation of restenosis, to a mammalian organism in need of such treatment.

In a more preferred embodiment of the present invention there is provided a method of preventing and treating restenosis in a mammalian organism, said method comprising a step of administering, in each 24 hour period a composition having a formulation which includes L-ascorbic acid, reduced form, in an amount of between about 6,500 and about 10,000 mg; calcium carbonate in an amount of between about 1,900 and about 3,000 mg, calcium D-pantothenate in an amount of between about 800 and about 1,200 mg; L-glutathione, reduced form, in an amount of between about 325 and about 500 mg; D,L-alpha tocopheryl acetate in an amount of between about 600 and about 1000 IU; thiamine hydrochloride in an amount of between about 250 and about 400 mg; pyridoxine hydrochloride in an amount of between about 135 and about 200 mg; beta carotene in an amount of between about 90 and about 150 mg; niacinamide in an amount of between about 100 and about 150 mg; niacin in an amount of between about 35 and about 50 mg; riboflavin in an amount of between about 25 mg and about 40 mg; cyanocobalamin in an about of between about 1,000 and about 1,500 micrograms, and cholecalciferol in an amount of between about 400 and about 650 IU.

In a most preferred embodiment in accordance with this aspect of the present invention there is provided a method as previously described where the formulation includes about 8,000 mg of L-ascorbic acid, about 2,500 mg of calcium carbonate, about 960 mg. of calcium D-pantothenate, about 400 mg. of L-glutathione, about 800 IU of D,L-alpha tocopheryl acetate, about 320 mg of thiamine hydrochloride, about 160 mg of pyridoxine hydrochloride, about 120 mg of beta carotene, about 120 mg of niacinamide, about 40 mg of niacin, about 32 mg of riboflavin, about 1,200 micrograms of cyanocobalamin, and about 500 IU of cholecalciferol.

It is also preferred, in accordance with this aspect of the present invention that the formulation is administered in four substantially equal dosages, each of which is administered between about 4 and about 7 hours apart.

The aforementioned methods result from the discovery that the administration of certain antioxidants, when provided to the body in sufficient quantity spaced throughout a 24-hour period, aid in the prevention and the treatment of restenosis following angioplasty. While not wishing to be bound by any particular theory of operation, it is believed that the presence of sufficient amounts of certain water soluble and fat soluble antioxidants will significantly reduce the formation of free radicals, particularly in tissue directly affected during angioplasty. It is further postulated that the presence of sufficient quantities of D,L-alpha tocopheryl acetate (Vitamin E), beta carotene, (which is a precursor of Vitamin A) and L-glutathione in a reduced form, inhibit the metabolic oxidative processes involved in the conversion of arachidonic acid in platelets and machrophage cells, thus resulting in the reduced formation of prostaglandins, several cytokines, PDGF and MDGF. This should reduce and retard the growth of restenosis. Vitamin C aids in the regeneration of the antioxidant ingredients thus maintaining their effectiveness between dosages.

While some of the aforementioned ingredients are available in common multi-vitamin supplements, they are not provided in the combinations or in the quantities believed to be necessary to provide for the treatment and prevention of restenosis as disclosed herein nor are they likely to be administered in a pattern sufficient to maintain their levels in the body consistently through a 24-hour period. Furthermore, there has been, apparently, no suggestion as to the use of these ingredients in any form or combination to prevent and to treat restenosis.

In accordance with another aspect of the present invention there is provided an advantageous composition which has been found to be particularly effective for use in the treatment and prevention of restenosis. The pharmaceutically active antioxidant containing composition includes: a formulation including L-ascorbic acid, reduced form, in an amount of between about 6,500 and about 10,000 mg; L-glutathione, reduced form, in an amount of between about 325 and about 500 mg; D,L-alpha tocopheryl acetate in an amount of between about 600 and about 1,000 IU; and beta carotene in an amount of between about 90 and about 150 mg; said composition capable of being administered in four substantially equal dosages throughout a single 24 hour period and said composition being effective in the prevention and treatment of restenosis in mammalian organisms in need thereof.

In a preferred embodiment in accordance with this aspect of the present invention, the pharmaceutically active antioxidant containing composition previously described includes about 8,000 mg of L-ascorbic acid; about 400 mg of L-glutathione, about 800 IU of D,L-alpha tocopheryl acetate; and about 120 mg of said beta carotene.

In accordance with another embodiment of the present invention, there is provided a pharmaceutically active antioxidant containing composition which includes a formulation having L-ascorbic acid, reduced form, in an amount of between about 6,500 and about 10,000 rag; calcium carbonate in an amount of between about 1,900 and about 3,000 mg, calcium D-pantothenate in an amount of between about 800 and about 1,200 mg; L-glutathione, reduced form, in an amount of between about 325 and about 500 mg; D,L-alpha tocopheryl acetate in an amount of between about 600 and about 1,000 IU; thiamine hydrochloride in an amount of between about 250 and about 400 mg; pyridoxine hydrochloride in an amount of between about 135 and about 200 mg; beta carotene in an amount of between about 90 and about 150 mg; niacinamide in an amount of between about 100 and about 150 mg; niacin in an amount of between about 35 and about 50 mg; riboflavin in an amount of between about 25 mg and about 40 mg; cyanocobalamin in an amount of between about 1,000 and about 1,500 micrograms, and cholecalciferol in an amount of between about 400 and about 650 IU; said composition capable of being administered in four substantially equal dosages throughout a single 24 hour period and said composition being effective in the prevention and treatment of restenosis in mammalian organisms in need thereof.

In a most preferred aspect of the present invention the aforementioned pharmaceutically active antioxidant containing composition has a formulation including about 8,000 mg of said L-ascorbic acid, about 2,500 mg of said calcium carbonate, about 960 mg. of said calcium D-pantothenate, about 400 mg. of said L-glutathione, about 800 IU of said D,L-alpha tocopheryl acetate, about 320 mg of said thiamine hydrochloride, about 120 mg of said beta carotene, about 160 mg of said pyridoxine hydrochloride, about 120 mg of said niacinamide, about 40 mg of said niacin, about 32 mg of said riboflavin, about 1,200 micrograms of said cyanocobalamin, and about 500 IU of said cholecalciferol.

The aforementioned compositions have been found to be particularly useful in the prevention and treatment of restenosis following angioplasty. They represent a delicate balance of ingredients which serve not only to reduce the number of free radicals formed in the area of angioplasty, but also to inhibit the metabolic oxidation of arachidonic acid. The more preferred formulations in accordance with the present invention also enhance the performance of the composition by recycling certain antioxidant ingredients in the formulation and by offering the formulation allowing for long term use. These compositions, when provided in sufficient dosage over a period of 24 hours have been found to be useful in the treatment and the prevention of restenosis.

DETAILED DESCRIPTION OF THE PREFERRED EMBODIMENT

It is preferred that the antioxidants of the present invention be provided in a form which is as nearly pure as possible. They should be present without noxious lubricants (sand, soaps, talc), fillers, colors, flavors, binders, dispersants or like adjuvants commonly employed as delivery excipients in the pharmaceutical industry. The antioxidant ingredients, as well as other ingredients in the formulation, may be administered individually, or in combination, in a pill or capsule form, in powdered form or in the form of a solution, slurry or dispersion. However, for convenience, and dosage consistency, as well as for assisting in the uniform administration of various dosages of the individual ingredients throughout a 24-hour period, it is advantageous that the ingredients described herein be admixed and administered together. Further, it is most preferred that the formulation of the present invention be provided in the form of a pill or capsule in that these forms provide the most protection of the various ingredients from airborn contaminants and humidity. As used herein, the terms "pill(s)" and "capsule(s)" are used interchangably. In the most preferred embodiment in accordance with the present invention, the composition is provided in a plurality of capsules. It is, of course, possible that one capsule containing all the ingredients be provided. However, due to the granular volume of the various ingredients such capsule would be difficult to swallow. Further, the glutathione and cyanocobalamin must be put into separate capsules to prevent the reductive chemical degradation of cyanocobalamin. Glutathione is a strong chemical reducing agent. Reductive chemical degradation of cyanocobalamin may result in the formation of reduced cyanocobalamin products that are thought to be toxic to the central nervous system.

Furthermore, it is advantageous that the fat soluble ingredients such as the D,L-alpha tocopheryl acetate and the beta carotene be separated from the water soluble ingredients as their respective encapsulation procedures may differ significantly.

One method which would allow for the production of capsules or dosage forms without requiring the use of the aforementioned excipients is disclosed in U.S. Pat. No. 4,454,125 which issued in the name of Demopoulos, and the text of which is hereby incorporated by reference. Specifically, the method of manufacture described therein may be used to produce dry powder formulations of various vitamins using Vitamin C (ascorbic acid) planar crystals as the sole lubricant in the manufacturing process. Such supplements are therefore free of the excipients previously described and can be ingested at high dosages, several times daily over a prolonged or indefinite period without noxious reactions or side effects which may follow high concentration of various manufacturing additives.

The pharmaceutically active antioxidant containing compositions of the present invention have a formulation which includes L-ascorbic acid in reduced form, L-glutathione, D,L-alpha tocopheryl acetate and beta carotene. In a preferred embodiment of the present invention, there is provided a pharmaceutically active antioxidant containing composition which includes L-ascorbic acid, reduced form, in an amount of between about 6,500 and about 10,000 mg; L-glutathione, reduced form, in an amount of between about 325 and about 500 mg; D,L-alpha tocopheryl acetate in an amount of between about 600 and about 1,000 IU; and beta carotene in an amount of between about 90 and about 150 mg; said composition capable of being administered in four substantially equal dosages throughout a single 24 hour period and said composition being effective in the prevention and treatment of restenosis in mammalian organisms in need thereof. Additionally provided ingredients may include calcium carbonate in an amount of between about 1,900 and about 3,000 mg, calcium D-pantothenate in an amount of between about 800 and about 1,200 mg; thiamine hydrochloride in an amount of between about 250 and about 400 mg; pyridoxine hydrochloride in an amount of between about 135 and about 200 mg; niacinamide in an amount of between about 100 and about 150 mg; niacin in an amount of between about 35 and about 50 mg; riboflavin in an amount of between about 25 mg and about 40 mg; cyanocobalamin in an amount of between about 1,000 and about 1,500 micrograms, and cholecalciferol in an amount of between about 400 and about 650 IU; said composition capable of being administered in four substantially equal dosages throughout a single 24 hour period and said composition being effective in the prevention and treatment of restenosis in mammalian organisms in need thereof. More preferably, these additional ingredients may be present in an amount of about 2,500 mg of the calcium carbonate, about 960 mg. of the calcium D-pantothenate, about 320 mg of the thiamine hydrochloride, about 160 mg of the pyridoxine hydrochloride, about 120 mg of the niacinamide, about 40 mg of the niacin, about 32 mg of the riboflavin, about 1,200 micrograms of the cyanocobalamin, and about 500 IU of the cholecalciferol.

It is important to note that these formulations are not meant as a replacement of those ingredients naturally produced in the body and/or consumed in the diet, but rather represent a supplement to normal blood levels.

A number of the aforementioned ingredients which may be included in formulations in accordance with the various embodiments of the present invention are described in Motschan, U.S. Pat. No. 4,619,829, the text of which is hereby incorporated by reference.

The physical and chemical characteristics of the tripeptide glutathione have been described in the Merck Index, 11th Ed., page 703, N-(N-L-gamma-glutamyl-L-cysteinyl) glycine, L-glutathione, glutathione-SH. Vitamin C has been described in the Merck Index, 11th Ed., page 130. The reduced form is preferred for us in accordance with the present invention.

Vitamin E, (D,L-alpha tocopheryl acetate) is broken down during digestion to yield alpha tocopherol which is the active antioxidant form. Unfortunately as a fat soluble vitamin, alpha tocopherol is probably not absorbed completely and a significant portion of the dosage ingested may be excreted. Thus it is important that the amount of Vitamin E provided in each dosage be higher than comparable dosages found in common vitamin supplements. Further, it is important that sufficient blood levels of alpha tocopherol be maintained and thus it is necessary to administer the formulation of the present invention in approximately equal periods throughout a 24-hour day. Approximately equal periods in the context of the present invention means that four dosages are contemplated, the administration of which is separated by no more than about seven and no less than about four hours, with the optimum being a separation of approximately six hours between each dosage. In general, the alpha tocopherol enters cell membranes including those of the mitochondria and serves as a lipoidal antioxidant scavenging hydroperoxyl and other oxy radicals. Vitamin E is also believed to interfere with the metabolic process involving arachidonic acid thereby inhibiting the continued accumulation of platelets and such cells as macrophages in the area of the artery subjected to angioplasty.

As is true with Vitamin E, the body's uptake of beta carotene is relatively slow and incomplete. Therefore the amounts of beta carotene and the manner in which it is administered are important. Fortunately, to combat restenosis the ideal administration regimen is similar to that of Vitamin E. Furthermore, there is an efficient regulatory system in the intestinal mucosa and the liver that prevents the over production of Vitamin A from its precursor, beta carotene. Thus the bulk of the administered beta carotene remains unchanged and serves as a lipoidal antioxidant that scavenges $\cdot$OOH (hydroperoxyl) and $^1O_2$ (delta singlet oxygen). There is, therefore, little or no possibility of hypervitaminosis. In addition, the beta carotene aids in the suppression of the metabolic oxidation of arachidonic acid.

It is known that if taken separately and in large doses, particularly doses exceeding 100 mg. for a period of 7-10 days, a slight yellow-orange discoloration of the skin may occur in some individuals. As the total daily amount increases up to 200-300 mg, a majority of normal, healthy individuals will notice some discoloration. This discoloration is usually first noticeable on the palms of the hands. The discoloration represents subcutaneous and cutaneous storage for beta carotene. This is not a toxic reaction and only rarely will there be generalized discoloration at doses below 200–300 mg.

As administered to angioplasty patients in the context of the present invention and in combination with the other ingredients discussed and disclosed, the likelihood of the development of generalized yellow-orange skin color is reduced. Candidates for coronary angioplasty are probably compromised with respect to their tissue antioxidant levels, and as such will require the extra beta carotene. If such color should develop, it will fade within 5–7 days after discontinuation of the treatment.

The combination of the four ingredients described previously, namely beta carotene, L-ascorbic acid in reduced form, L-glutathione in reduced form and D,L-alpha tocopheryl acetate; are believed to provide for the prevention and/or treatment of restenosis. As previously described, it is believed that these ingredients, except the Vitamin C help shut down the formation of free radicals and interrupt various processes which serve to increase the formation of restenosis. The Vitamin C is believed to aid in regenerating the aforementioned antioxidants such that they are reused to further prevent free radical formation and the formation of restenosis. Other ingredients are also useful for regeneration of the aforementioned D,L-alpha tocopheryl acetate, beta carotene, and L-glutathione as will be discussed below, and are also useful in the general treatment of angioplasty patients.

Cyanocobalamin is an important co-factor in membrane biosynthesis, separate and aside from its role in nucleic acid metabolism. In membranes, it fosters the methylation of phospholipids, to yield positively charged quartenary ammonium moleties at the hydrophilic surfaces. This is important in fostering a higher density of positive changes on the surfaces of platelets and such cells as macrophages. It is believed that such a higher density of positive charges will decrease the excess accumulation of platelets and macrophage cells at the angioplasty site since similarly charged particles are physically kept apart.

Cyanocobalamin is sometimes given by injection in dosages of 1000 micrograms to overcome poor absorption from the gastro intestinal track. Such treatments are most common in the elderly who may lack certain factors which promote cyanocobalamin absorption. However, it has been found that if cyanocobalamin is administered in large enough doses ranging from about 200 to about 400 micrograms, and in pure crystalline form it will be absorbed by mass action, even if specific intrinsic factors which promote its absorption are present in low levels. The pure crystalline form of cyanocobalmin forms a very high local concentration in the micro-environment of the mucosal lining, thus creating mass action absorptive conditions. Cyanocobalamin is, in and of itself, non-toxic. However, if allowed to undergo certain chemical reductions during manufacture and storage, potentially harmful products may then form. For example, the careless mixing of cyanocobalamin with iron or ascorbic acid will result in formation of potentially harmful reduced forms. The methods of formulation discussed in U.S. Pat. No. 4,454,125, when utilized, avoid such unwanted consequences.

Cholecalciferol (Vitamin D) is added to enhance calcium absorption. It is unlikely that too much calcium will be consumed. Calcified tissue deposits do not occur until the daily consumption regularly exceeds 3,000 or 4,000 mgs. of calcium.

Calcium, when added as calcium carbonate, not only helps prevent bone decay, but also provides a buffer to mitigate gastro-intestinal distress caused by the continued consumption of, for example, ascorbic acid. It also assures adequate calcium in cardiac patients who have generally been put on low-fat, low-dairy diets. Adequate calcium intake has also been found to aid in lowering elevated blood pressure.

The mixtures of ingredients in the present formulation, in addition to providing the functions previously defined, also provide metabolic co-factors necessary for recycling exhausted antioxidants. For example, chemically simple antioxidants such as glutathione are exhausted after neutralizing a free radical. However, if hydrogen is supplied, then the antioxidant will be recycled into an active form again via regenerative systems involving a hydrogen transport carrier such as NADH and NADPH and enzymes such as glutathione reductase.

Metabolic co-factors such as the B vitamins, thiamine, niacin, niacinamide, riboflavin, pantheonic acid and pyridioxine and certain other water soluble vitamins assist in the production of more hydrogen, systemically, as well as assisting in the transportation of hydrogen throughout the cells. For this reason, these co-factors may be useful and provide a symbiotic and regenerative effect.

The present invention also includes a method for preventing and treating restenosis in a mammalian organism, the method including the step of administering, in each 24 hour period, a composition including L-glutathione, in reduced form, D,L-alpha tocopheryl acetate, L-ascorbic acid in reduced form and beta carotene. Each of the compounds of the formulation shall be present in an amount effective to treat and to prevent the formation of restenosis, to a mammalian organism in need of such treatment. In a preferred embodiment the formulation includes between about 6,500 and about 10,000 mg of the L-ascorbic acid; between about 325 and about 500 mg of the L-glutathione, between about 600 and about 1,000 IU of the D,L-alpha tocopheryl acetate and about 100 to about 150 mg of the beta carotene. Ingredients which may also be useful in the formulation of the present invention include calcium carbonate, calcium D-pantothenate, thiamine hydrochloride, pyridoxine hydrochloride, niacinamide, niacin, riboflavin, cyanocobalamin, cholecalciferol.

In a more preferred embodiment, the method of preventing and treating restenosis includes the use of a composition having a formulation which includes: calcium carbonate in an amount of between about 1,900 and about 3,000 mg, calcium D-pantothenate in an amount of between about 800 and about 1,200 mg; thiamine hydrochloride in an amount of between about 250 and about 400 mg; pyridoxine hydrochloride in an amount of between about 135 and about 200 rag; niacinamide in an amount of between about 100 and about 150 rag; niacin in an amount of between about 35 and about 50 rag; riboflavin in an amount of between about 25 mg and about 40 mg; cyanocobalamin in an about of between about 1,000 and about 1,500 micrograms, and cholecalciferol in an amount of between about 400 and about 650 IU.

In a most preferred method in accordance with the present invention the formulation includes about 8,000 of L-ascorbic acid, in reduced form about 2,500 mg. of said calcium carbonate, about 960 mg. of said calcium D-pantothenate, about 400 mg. of said L-glutathione, in reduced form, about 800 IU of said D,L-alpha tocopheryl acetate, about 320 mg of said thiamine hydrochloride, about 160 mg of said pyridoxine hydrochloride, about 120 mg of said beta carotene, about 120 mg of said niacinamide, about 40 mg of said niacin, about 32 mg of said riboflavin, about 1,200 micrograms of said cyanocobalamin, and about 500 IU of said cholecalciferol.

Advantageously, the composition, in accordance with the present method is administered in four substantially equal dosages, each of the dosages being administered about four and seven hours apart and most preferably six hours apart. As previously discussed it has been found that an administration regimen which includes the use of relatively high concentrations of each of the aforementioned ingredients essentially evenly distributed throughout an entire day can, over time, assist in the prevention and treatment of restenosis. Administration may be intravenous, parenteral, rectal, or oral with oral being most preferred.

Most of the components of the antioxidant formulation of the present invention are highly water soluble and absorption starts immediately after dissolution of the gelatin capsules, if there are minimal gastric contents. Within 20 minutes approximately one half of the water soluble components are absorbed through the gastric mucosa on an empty stomach. The remainder of the water soluble material is taken up within the next 30 minutes. The beta carotene, alpha tocopherol, calcium and cholecalciferol are absorbed in the small intestine over a period of one to three hours, depending on gastric contents and gastric emptying time. The tripeptide, glutathione, is absorbed as the tripeptide from the intestines.

Excretion patterns vary as a function of fluid intake, dietary composition, and degree of physical activity. Ascorbic acid taken in these dosages will achieve peak blood levels within approximately 1 to 1.5 hours declining significantly thereafter, in the subsequent four to six hours. The principal route of excretion is via the urine as astorbate. The metabolic cofactors follow a similar, but somewhat slower urinary excretion pattern.

The antioxidant formulation is too acidic for most patients with an active gastric or duodenal ulcer to ingest orally. In addition, the use of the formulation by patients with Parkinson's disease who are being treated with L-DOPA alone is contraindicated because pyridoxine counteracts L-DOPA and decreases its effects; if a Parkinsonian patient is being treated with one of the newer drug formulations, then these antioxidant formulations can be used freely.

The following non-limiting examples illustrate certain aspects of the present invention (the formulation for each day was administered in four substantially equal dosages contained in capsules packaged within small plastic packets):

EXAMPLE I

PATIENT #4 SFHI#3200

Patient is a 65 year old physician who had a history of elevated cholesterol, had been a smoker, and had a strong family history of heart disease. The patient was not having chest pain, but exercise treadmill revealed significant electrocardiographic changes suggestive of impaired blood flow. Subsequent thallium exercise imaging showed marked ischemia in the anterior and lateral walls of the heart muscle. In July of 1988, he underwent cardiac catheterization. A #8F USCI sheath was introduced into the right femoral artery and a standard diagnostic catheter was advanced. Selective injections revealed a severe narrowing in the proximal left anterior descending artery, and a complex stenosis involving the branch point between the left anterior descending and the first diagonal branch. It was decided to go ahead with angioplasty, using the "kissing balloon" technique, placing two balloons in the artery, one down the left anterior descending and the other down the diagonal branch. Another #8 USCI sheath was introduced into the left femoral artery. A #8 French Judkins Left-4 was introduced via the right femoral artery into the ascending aorta. 10,000 units of heparin were administered. Difficulty was encountered seating the catheter properly, and it was exchanged for a 3.5 guiding catheter which successfully cannulated the left main. A Judkins Left 3.5 guiding catheter was advanced through the left femoral artery, but again, difficulty in seating the catheter in the left main was encountered. After several catheters failed, the #8 sheath in the left femoral artery was replaced with a #9 sheath. An 8.3 long Stertzer guide was introduced, but did not seat properly. Several Amplatz catheters were tried, but none was successfully seated. A decision was made to gain entry through the right brachial artery. The area was prepped and anesthetized with 2% lidocaine with epinephrine. A cutdown was performed and the brachial artery isolated. An 8.3 Meta-Stertzer guide catheter was introduced through the right brachial entry and was also unsuccessful, followed by a 2-inch bent-tip guiding catheter that was properly seated in the left main coronary artery. A 3.0 mm Profile Plus was introduced via the femoral artery and advanced into the left anterior descending artery, through the stenosis, and into the distal vessel. A 2.5 mm Profile Plus was advanced through the brachial entry. However, it could not successfully cross the lesion and was exchanged for a 2.0 mm Profile plus, which did pass into the diagonal branch. Four balloon inflations were performed at 9 atmospheres of pressure for 60 seconds in the left anterior descending artery along the bifurcation point and distal to the site. 6 inflations at 10 atmospheres for 40 seconds were undertaken in the diagonal branch with the 2.0 balloon. 5 more inflations were performed in the left anterior descending artery. Final arteriograms were taken, demonstrating a good angiographic result (less than 15% narrowing) at the bifurcation site and in the diagonal branch. All equipment was removed. The patient was maintained on heparin overnight. Because of the complexity of the procedure, the patient was discharged on antioxidant therapy 4 times per day. 9 months later, cardiac catheterization revealed totally normal arterial flow through the left anterior descending and diagonal branch. The patient had been taking the full dose (4 packets per day) of antioxidants during the time period. A thalium exercise test was performed 5 months after the angiographic re-evaluation and it demonstrated completely normal blood perfusion in the myocardial tissue served by the left anterior descending system.

EXAMPLE 2

PATIENT #3 SFHI#3034

Patient is a 49 year old male who had an anterior infarction in March of 1988. The patient had no significant risk factors for coronary artery disease. Standard coronary arteriography was performed following usual sterile preparation. A sheath was inserted into the femoral artery and a diagnostic catheter advanced to the left coronary artery. Selective injections of radiographic dye revealed severe 95% narrowing in the proximal portion of the left anterior descending artery, a 90% narrowing in the midzone of the left circumflex artery and a 90% narrowing of the orifice of the diagonal branch. 10,000 units of heparin were administered. A 2.5 mm low profile balloon catheter system with a 0.014 flexible steerable 98% coated Teflon coated guidewire was assembled in the usual manner, passed through the FL-4 guide and advanced into the left circumflex artery. Serial inflations were carried out at 9 atmospheres of pressure, achieving full balloon inflation, and several low pressure dilations were performed. Dye injections demonstrated an excellent result. The equipment was removed, and a new wire inserted for the approach to the left anterior descending artery. The wire was carefully passed through the proximal stenosis of the left anterior descending and on to the origin of the diagonal branch. The wire and balloon crossed this stenosis and the balloon was inflated to 7 atmospheres of pressure for several inflations. Injections revealed excellent results, and the balloon was withdrawn to the origin of the left anterior descending and inflated to 10 atmospheres of pressure for 60 seconds. The balloon was deflated and removed, and replaced with a 3.0 PVC balloon to achieve a larger lumen opening. This balloon catheter was advanced and inflated to 9 atmospheres of pressure for 60 seconds. Multiple injections demonstrated an excellent result at the site and final post angioplasty radiographic injections revealed excellent flow through all dilated areas, reducing all stenosis to less than 15% narrowing. Because of the extent of coronary disease and the presence of an ostial lesion (which carries a high risk of restenosis), the patient was discharged on low doses of aspirin (324 mg, twice a week) and antioxidant therapy 4 times per day. The patient was without symptoms at a follow-up 9 months later, but his evaluation included a coronary angiogram. The injections showed continued patency at all sites dilated at the initial angioplasty. The patient reported taking the antioxidant therapy at the prescribed 4 packet per day dose level.

EXAMPLE 3

PATIENT #2 SFHI #3171

Patient is a 58 year old female admitted in February of 1988 for an anterior myocardial infarction. She had elevated cholesterol (289) and triglycerides (370), with a family history of heart disease. In July of 1988 she was admitted for chest pain and a coronary arteriography was performed using standard procedure. Injection of radiographic dye revealed a 100% proximal blockage of the left anterior descending coronary artery. 10,000 units of heparin were administered. A 3.25 mm Profile Plus balloon dilatation catheter was advanced over a 0.014 flexible wire. The wire was able to pass the total blockage and the balloon was advanced successfully over the wire. 40,000 units of Urokinase (a thrombolytic agent) were infused through the catheter. Since significant thrombus was visualized, the decision was made to leave the catheters in place and infuse Urokinase directly into the coronary artery at a rate of 1000 units per minute for 24 hours. Heparin was also infused at 500 units per hour. The patient remained in intensive care and was returned to the cardiac catheterization laboratory the next day. Angiographic evaluation demonstrated that a significant portion of the thrombus had resolved. A 2.5 mm Profile Plus balloon catheter was advanced into the area of stenosis and successfully dilated at 6 atmospheres of pressure for 60 seconds. Three further dialations were performed along the diffusely diseased segment of the artery. Next, the balloon catheter was exchanged for a larger 3.25 mm Profile Plus. Two additional inflations were performed at 8 atmospheres of pressure for 55 seconds each. Repeat anglographic views demonstrated improvement of the proximal segment of the artery, but there was some residual thrombus near the point where the first diagonal branch originates from the left anterior descending artery. The decision was made to remove all equipment and transfer the patient to intensive care, administering intravenous urokinase and heparin, and re-evaluate in 24 hours. On the following day a standard coronary anglogram was performed, revealing only mild stenosis (30%) in the proximal region of the left anterior descending artery. All thrombus had dissolved. The patient was discharged on reduced aspirin dose (324 mg, the amount in one regular aspirin tablet, twice a week) and antioxidant therapy (4 packets per day) because of the extremely high risk for restenosis of the diffusely diseased left anterior descending artery. Follow-up 6 months later showed a normal blood distribution on thallium exercise test, suggesting patent vessels. The patient had no symptoms and reported taking antioxidants at the prescribed level of 4 packets per day. Her cholesterol had dropped to 233 and triglycerides to 172. Clinical evaluation 9 months later suggested that no restenosis had occurred. The patient continued without anginal symptoms.

EXAMPLE 4

PATIENT #5 SFHI#3191

The patient is a 59 year old male who had been experiencing chest pain on exertion about 2 weeks prior to evaluation. He was a heavy smoker, with an extremely high cholesterol (300) and a history of hypertension. Cardiac catheterization was performed via a sheath in the right femoral artery. In anticipation of a possible "kissing balloon" procedure, the right brachial artery was prepared using standard cutdown technique. A Stertzer guiding catheter was used to visualize the arterial system. Selective injection revealed mild disease in the left main stem artery and a 70% narrowing in the mid portion of the right coronary artery, extending to the origin of the apical marginal branch. 10,000 units of heparin were administered. After several attempts at advancing a 2.0 probe through the apical marginal branch, a straightforward approach with a 3.5 mm Profile Plus balloon and 0.014 inch flexible steerable wire was utilized. Multiple dilatations were carried out at 9 atmospheres in three separate segments of the right coronary artery. Blood flow through the vessel was excellent at the end of the procedure. The patient was taken to the recovery area where the brachial artery was sewn and intravenous heparin therapy was begun. The disease in the left arterial system was not addressed at this time. The patient was discharged on antioxidant therapy (4 packets per day) because of his multivessel disease, which put him at higher risk for recurrence. 9 months after angioplasty, the patient was symptom free. An exercise thallium study demonstrated normal flow to the myocardial tissue served by the right coronary artery. The patient reported that he took approximately 3 packets of antioxidant per day.

EXAMPLE 5

PATIENT #6 SFHI#3175

The patient is a 67 year old man who had severe chest pain and heaviness of his left arm while on vacation. He was admitted into the hospital at the time with an abnormal electrocardiogram suggestive of posterior myocardial infarction. The patient had a history of hypertension, but no elevated cholesterol or triglycerides, and no family history of heart disease. The groin was punctured under local anesthetic and a Myler catheter sheath placed in the right femoral artery through which the guiding catheter was advanced to the left coronary system. Selective injections revealed a 75% narrowing at the proximal portion of the left circumflex artery and a tandem lesion in the distal portion of at least 90% stenosis. 10,000 units of heparin were administered. An LTS 3.0 mm balloon catheter was advanced across the narrowings and sequential inflations were performed at 11 atmospheres pressure for approximately 40 seconds over the entire length of the artery. Although flow results at the end of angioplasty were good there was a significant dissection of the arterial wall. The patient was put on heparin for 24 hours with the Myler catheter sheath left in place. When the patient returned to the catheterization laboratory the next day, selective angiography demonstrated that the proximal circumflex site had acutely renarrowed to 90% (such acute renarrowing differs from the 3–6 month course of restenosis; this acute renarrowing generally reflects arterial spasm, and local acute accumulations of platelets that release vasospastic substances such as thromboxane $A_2$. A 0.014 guidewire and 40 mm long 3.5 mm LPS dilatation catheter were advanced across the narrowing. The balloon was dilated at 10 atmospheres of pressure. The stenosis was reduced to less than 10%. Flow at the end of the angioplasty appeared to be good, and the dissection from the previous day had been resolved. Because of the difficulty of the procedure and the diffuse nature of the disease, the patient was discharged on 4 packets per day of antioxidant therapy and low-dose aspirin (324 mg twice a week). At a 4 month follow-up, the patient was asymptomatic and had normal thallium exercise treadmill testing. He reported continuing on the prescribed antioxidant regimen. The patient was still free from symptoms at 1 year post the initial angioplasty.

EXAMPLE 6

One dosage consisted of two yellow capsules, one white capsule and two red capsules.

190,000 yellow capsules were prepared as follows:

22.8 kilograms of calcium pantothenate (Hoffman-LaRoche, Nutley, N.J. Lot #909525) was placed in a 10 cubic foot equal arm Patterson-Kelly V-blender. Four more components were subsequently added in the following order:
1. 8.51 kilograms thiamine-HCl (Hoffman-LaRoche, lot #809709).
2. 4.62 kilograms pyridoxine-HCl (EM Industries, Hawthorne, N.Y. lot #TF193524).
3. 760 grams riboflavin (Chemical Dynamics, South Plainfield, N.J. lot #141418).
4. 152 kilograms ascorbic acid (fine granular, Hoffman-LaRoche lot #276119).

These components were mixed for 20 minutes in order to properly coat the planar ascorbic acid crystals with the pure crystalline B vitamins.

A separate trituration consisting of 2.85 kilograms niacin (Hoffman-LaRoche lot #165039), 950 grams niacinamide (Hoffman-LaRoche lot #804109) and 28.5 grams crystalline cyanocobalamin (EM Industries lot #8834100) was prepared and mixed for 5 minutes in a 1 cubic foot Hobart mixer. The triturate was then added to the mixture in the Patterson-Kelly mixer and blended for 45 minutes. All mixing was done at temperatures between 65°–68° F and humidity between 30–50%. The mixture was stored in 50-kilogram drums lined with a polyethylene bag until needed for encapsulation.

Yellow capsules were made as follows:

The mixture was loaded into the powder hopper of an automatic Zanasi AZ-20 capsule filling machine (Soteco, Fairfield, N.J., serial #66188) in 20 kilogram aliquots, replacing as necessary. Size -00- two-piece gelatin capsules (Pharmaphil, Windsor, Canada lot #J8-0937-4S) were filled with 1.0133 grams of mixture per capsule. To achieve this, microfinish-coated dosators (Isometrics, Edison, N.J.) were set to 2.1 centimeters and the capsule compression to -000-. Powder pan was set to 5.2 centimeters. Humidity was maintained between 30–50%, and temperature between 65°–68° F. Capsules were produced at a rate of 14,300 capsules per hour for an 8 hour period, after which it was necessary to thoroughly wash and dry the microfinish-coated bushings and dosators to prevent sticking. Capsules do not require further surface cleansing.

Sufficient mixture to prepare 171,000 white capsules was prepared as follows:

68.4 kilograms ascorbic acid (fine granular, Hoffman-LaRoche lot #276119) was placed in a 10 cubic foot equal arm Patterson-Kelly V-blender. Three more ingredients were added in the following order:
1. 17.1 kilograms L-glutathione, reduced (Technochem, Pompton Plains, N.J. lot #BHF-104).
2. 27.9 grams cholecalciferol beadlets (Hoffman-LaRoche lot #810066).
3. 106.87 kilograms calcium carbonate ("Vercode 150" manufactured by Omya, of Vermont lot #0024).

The mixture was blended for 45 minutes and then stored in 50-kilogram drums lined with polyethylene bags prior to encapsulation.

The encapsulation was performed on a semiautomatic Parke-Davis Type 8 capsule filling machine (Capsugel, Greenwood, S.C.). Approximately 3 kilograms of mixture was loaded into the powder hopper, and this was repeated when necessary. To achieve a proper fill of 1.125 grams per capsule, the machine speed was adjusted to setting B-2. Two hundred and forty size -00- capsules were fed into a two-layer capsule ring in a rectified orientation. The upper half of the ring was lifted after capsules were separated by rotation of the ring across a vacuum slot. The capsule bottoms were then filled with mixture by drawing the powder hopper across the ring while it rotated at the properly adjusted speed setting. The upper half of the ring containing the capsule tops was then replaced and the capsule halves were joined by insertion of the ring into a compressed air-driven peg assembly. The capsules were then ejected through the ring holes and fell onto a downward-sloping vibrating track for gross removal of surface powder. Capsules were then placed in a wire basket and salted three times with sodium chloride (Sureflow Fineflake brand, Landmark Corp., Northhaven, Conn.) to remove additional surface powder. Capsules were filled at a rate of 7,000 capsules per hour for an 8 hour shift, after which the rings were thoroughly washed and dried.

Soft gel encapsulation of the D,L- alpha tocopheryl acetate and beta carotene to form the red capsules was achieved as follows:

Due to the instability of pure beta carotene crystals in air and their known stability in oils, such capsules have in the past been made using beta carotene suspended in vegetable oils. However, these oils easily rancidify during storage, and the radical species formed through this process will oxidize the beta carotene, rendering it useless as an antioxidant. This problem has been solved by our use of pure D,L-alpha tocopheryl acetate (vitamin E acetate) as the suspension medium for our beta carotene soft gel capsules. Thus the D,L-alpha tocopheryl acetate serves a dual purpose. It both protects the beta carotene from oxidative degradation due to its relative insensitivity to light an oxygen damage, and serves as a source of vitamin E in the therapeutic mixture.

Softgel capsules were chosen as the preferred method of encapsulation for their convenience and their property of being an excellent oxygen barrier. The softgel capsules were manufactured to our specifications by Pharmacaps, Inc., Elizabeth, N.J. For the production of 1 million capsules, 15 kilograms of pure crystalline beta carotene (BASF, Parsippany N.J. lot #98177) was blended for one hour with 100 kilograms of pure D,L-alpha tocopheryl acetate (BASF lot #98193) in a stainless steel mixing vessel. The mixture was precision milled, sieved and deaerated. Samples were drawn from the resulting paste for laboratory analysis to test homogeneity. The preparation was then transferred to stainless steel containers and stored until needed for encapsulation.

Encapsulation into soft gel capsules was accomplished using techniques known in the art. Liquid pharmaceutical USP grade gelatin containing glycerin as plasticizer was fed to a rotary die encapsulating machine through two temperature controlled dispensing units which cast the material on an air-cooled rotating drum forming two continuous gelatin ribbons of controlled thickness. The moving ribbons passed between two precision #2 oval die rolls, and the beta carotene-alpha tocopheryl acetate paste described above was pumped through orifices in a heated wedge riding on the gelatin. As the paste left the wedge, portions of gelatin ribbon were forced into pockets on each die roll. The filled capsule halves were then sealed and cut from the ribbon by rotating opposed dies. Each finished capsule contained 115 milligrams of the paste.

The capsules were washed with hexane to remove the pharmaceutical lubricant used on the gelatin ribbon, and then dried in a rotating drier with infra red heating units. The capsules were then spread on trays for a drying cycle of 24 hours and stored in polyethylene bags after inspection.

Drug interactions with these antioxidants have not occurred. The various patients were receiving a range of common prescription drugs including cardiac drugs, antibiotics, gastro-intestinal tract pharmaceuticals, bronchodilators, psychiatric agents, anti-histamines, alcohol, anticonvulants and so on. Drug interactions may occur, however, in patients using Dilantin or L-DOPA, principally because of pyridoxine. The newer formulations of L-DOPA are not interfered with by pyridoxine. This leaves a caution for the physician prescribing Dilantin and these antioxidants.

The particular antioxidant treatment regimen revealed here does not lead to hemorrhage, a bleeding tendency, increased infection, or any detectable organ toxicity. It is safe for patients who have had angioplasty, or coronary artery surgery, and/or thrombolysis prior to the commencement of therapy. The antioxidant combination is compatible with all categories of cardiac drugs, including: digitalis preparations; anti-arrhythmics; calcium channel blockers; anti-anginals; vasodilators; anti-coagulants; beta blockers, diuretics; anti-hypertensives; anti-platelet agents; cholesterol-lowering drugs. There are no known drug interactions other than the two cited (Dilantin and L-DOPA), and there are no incompatibilities with general anesthetics.

As these and other variations of the features described above can be used without departing from the present invention, the foregoing description of the preferred embodiment should be taken the way of illustration rather than the way of limitation of the invention as defined in the claims.

I claim:

1. A pharmaceutically active antioxidant containing composition consisting essentially of a formulation including L-ascorbic acid, reduced form, in an amount of between about 6,500 and about 10,000 mg; L-glutathione, reduced form, in an amount of between about 325 and about 500 mg; D,L-alpha tocopheryl acetate in an amount of between about 600 and about 1,000 IU; and beta carotene in an amount of between about 90 and about 150 mg; said composition capable of being administered in four substantially equal dosages throughout a single 24 hour period and said composition being effective in the prevention and treatment of restenosis in mammalian organisms in need thereof.

2. The pharmaceutically active antioxidant containing composition of claim 1, wherein said formulation includes about 8,000 mg of said L-ascorbic acid; about 400 mg of said L-glutathione, about 800 IU of said D,L-alpha tocopheryl acetate; and about 120 mg of said beta carotene.

3. The pharmaceutically active antioxidant containing composition of claim 2, wherein each of said four substantially equal dosages includes a plurality of capsules with said D,L-alpha tocopheryl acetate and said beta carotene being separated from the remainder of said formulation.

4. A pharmaceutically active antioxidant containing composition consisting essentially of a formulation including L-ascorbic acid, reduced form, in an amount of between about 6,500 and about 10,000 mg; calcium carbonate in an amount of between about 1,900 and about 3,000 mg, calcium D-pantothenate in an amount of between about 800 and about 1,200 mg; L-glutathione, reduced form, in an amount of between about 325 and about 500 mg; D,L-alpha tocopheryl acetate in an amount of between about 600 and about 1,000 IU; thiamine hydrochloride in an amount of between about 250 and about 400 mg; pyridoxine hydrochloride in an amount of between about 135 and about 200 mg; beta carotene in an amount of between about 90 and about 150 mg; niacinamide in an amount of between about 100 and about 150 mg; niacin in an amount of between about 35 and about 50 mg; riboflavin in an amount of between about 25 mg and about 40 mg; cyanocobalamin in an amount of between about 1,000 and about 1,500 micrograms, and cholecalciferol in an amount of between about 400 and about 650 IU; said composition capable of being administered in four substantially equal dosages throughout a single 24 hour period and said composition being effective in the prevention and treatment of restenosis in mammalian organisms in need thereof.

5. The pharmaceutically active antioxidant containing composition of claim 4, wherein said formulation includes about 8,000 mg of said L-ascorbic acid, about 2,500 mg of said calcium carbonate, about 960 mg. of said calcium D-pantothenate, about 400 mg. of said L-glutathione, about 800 IU of said D,L-alpha tocopheryl acetate, about 320 mg of said thiamine hydrochloride, about 160 mg of said pyridoxine hydrochloride, about 120 mg of said beta carotene, about 120 mg of said niacinamide, about 40 mg of said niacin, about 32 mg of said riboflavin, about 1,200 micrograms of said cyanocobalamin, and about 500 IU of said cholecalciferol.

6. The pharmaceutically active antioxidant containing composition of claim 5, wherein each of said four substantially equal dosages includes a plurality of capsules with said D,L-alpha tocopheryl acetate and said beta carotene being separated from the remainder of said formulation.

7. The pharmaceutically active antioxidant containing composition of claim 5, wherein each of said four substantially equal dosages includes a plurality of capsules with said L-glutathione being separated from said cyanocobalamin.

8. A method of preventing and treating restenosis in mammalian organisms, said method comprising the step of administering, in each 24 hour period, a formulation including the compounds L-ascorbic acid in reduced form, L-glutathione in reduced form, D,L-alpha tocopheryl acetate, and beta carotene, each of said compounds of said formulation being present in an amount effective to treat and to prevent the formation of restenosis, to a mammalian organism in need of such treatment.

9. The method of preventing and treating restenosis of claim 8; wherein said L-ascorbic is provided in an amount of between about 6,500 and about 10,000 mg; said L-glutathione is present in an amount of between about 325 and about 500 mg; said D,L-alpha tocopheryl acetate is present in an amount of between about 600 and 1,000 IU; and said beta carotene in an amount of between about 100 and 150 mg.

10. The method of preventing and treating restenosis of claim 9; wherein said L-ascorbic acid is provided in an amount of about 8,000 mg, said L-glutathione is present in an amount of about 400 mg, said D,L-alpha tocopheryl acetate is present in an amount of 800 IU, and said beta carotene is present in an amount of about 120 mg.

11. The method of claim 8, wherein said formulation is administered in four substantially equal dosages, each of said dosages being administered between about 4 and about 7 hours apart.

12. The method of preventing and treating restenosis of claim 11, wherein each of said four substantially equal dosages includes a plurality of capsules with said D,L-alpha tocopheryl acetate and said beta carotene being separated from the remainder of said formulation.

13. A method of preventing and treating restenosis in a mammalian organism, said method comprising the step of administering, in each 24 hour period, a formulation which includes L-ascorbic acid in reduced form, calcium carbonate, calcium D-pantothenate, L-glutathione in reduced form, D,L-alpha tocopheryl acetate, thiamine hydrochloride, pyridoxine hydrochloride, beta carotene, niacinamide, niacin, riboflavin, cyanocobalamin, cholecalciferol, each of the compounds of said formulation being present in an amount effective to treat and to prevent the formation of restenosis, to a mammalian organism in need of such treatment.

14. The method of claim 13 wherein said formulation includes L-ascorbic acid, reduced form, in an amount of between about 6,500 and about 10,000 mg; calcium carbonate in an amount of between about 1,900 and about 3,000 mg, calcium D-pantothenate in an amount of between about 800 and about 1,200 mg; L-glutathione, reduced form, in an amount of between about 325 and about 500 mg; D,L-alpha tocopheryl acetate in an amount of between about 600 and about 1000 IU; thiamine hydrochloride in an amount of between about 250 and about 400 mg; pyridoxine hydrochloride in an amount of between about 135 and about 200 mg; beta carotene in an amount of between about 90 and about 150 mg; niacinamide in an amount of between about 100 and about 150 mg; niacin in an amount of between about 35 and about 50 mg; riboflavin in an amount of between about 25 mg and about 40 mg; cyanocobalamin in an about of between about 1,000 and about 1,500 micrograms, and cholecalciferol in an amount of between about 400 and about 650 IU.

15. The method of claim 14 wherein said formulation includes about 8,000 mg of L-ascorbic acid, about 2,500 mg of said calcium carbonate, about 960 mg. of said calcium D-pantothenate, about 400 mg. of said L-glutathione, about 800 IU of said D,L-alpha tocopheryl acetate, about 320 mg of said thiamine hydrochloride, about 160 mg of said pyridoxine hydrochloride, about 120 mg of said beta carotene, about 120 mg of said niacinamide, about 40 mg of said niacin, about 32 mg of said riboflavin, about 1,200 micrograms of said cyanocobalamin, and about 500 IU of said cholecalciferol.

16. The method of claim 13, wherein said formulation is administered in four substantially equal dosages, each of said dosages being administered between about 4 and about 7 hours apart.

17. The method of preventing and treating restenosis of claim 16, wherein each of said four substantially equal dosages includes a plurality of capsules with said D,L-alpha tocopheryl acetate and said beta carotene being separated from the remainder of said formulation.

18. The method of preventing and treating restenosis of claim 16, wherein each of said four substantially equal dosages includes a plurality of capsules with said L-glutathione being separated from said cyanocobalmin.

* * * * *

UNITED STATES PATENT AND TRADEMARK OFFICE
CERTIFICATE OF CORRECTION

PATENT NO. : 5,326,757  
DATED : July 5, 1994  
INVENTOR(S) : Demopoulos

Page 1 of 3

It is certified that error appears in the above-identified patent and that said Letters Patent is hereby corrected as shown below:

Column 1, line 7, "This is a continuation division of" should read --This is a continuation of--.

Column 3, line 23, "4,784842" should read --4,784,842--.

Column 4, line 46, "about of" should read --amount of--.

Column 5, line 60, "10,000 rag;" should read --10,000 mg;--.

Column 9, line 37, "moleties" should read --moieties--.

Column 9, line 42, "excess" should read --excess--.

Column 9, lines 55-56, "cyanocobalmin" should read --cyanocobalamin--.

Column 10, line 59, 200 rag;" should read --200 mg;--.

UNITED STATES PATENT AND TRADEMARK OFFICE
CERTIFICATE OF CORRECTION

PATENT NO. : 5,326,757
DATED : July 5, 1994
INVENTOR(S) : Demopoulos

It is certified that error appears in the above-identified patent and that said Letters Patent is hereby corrected as shown below:

Column 10, lines 60-61, "150 rag;" should read --150 mg;--.

Column 10, line 62, "50 rag;" should read --50 mg;--.

Column 10, line 63 "in an about of" should read --in an amount of--.

Column 11, line 43, "astorbate" should read --ascorbate--.

Column 14, line 6, "dialations" should read --dilations--.

Column 14, lines 10-11, "anglographic" should read --angiographic--.

Column 14, line 18, "anglogram" should read --angiogram--.

Column 15, line 50, "1 year post" should read --1 year past--.

UNITED STATES PATENT AND TRADEMARK OFFICE
CERTIFICATE OF CORRECTION

PATENT NO. : 5,326,757
DATED : July 5, 1994
INVENTOR(S) : Demopoulos

It is certified that error appears in the above-identified patent and that said Letters Patent is hereby corrected as shown below:

Column 17, line 20, "light an oxygen" should read --light and oxygen--.

Column 20, lines 58-59, "cyanocobalmin" should read --cyanocobalamin--.

Signed and Sealed this

Twenty-seventh Day of September, 1994

BRUCE LEHMAN

Attest:

*Attesting Officer*

*Commissioner of Patents and Trademarks*